(12) United States Patent
Hansen

(10) Patent No.: US 8,889,362 B2
(45) Date of Patent: Nov. 18, 2014

(54) CELL CLASSIFICATION SYSTEM

(75) Inventor: Peter W. Hansen, Canaan, NY (US)

(73) Assignee: Point Care Technologies, Marlborough, MA (US)

( * ) Notice: Subject to any disclaimer, the term of this patent is extended or adjusted under 35 U.S.C. 154(b) by 1160 days.

(21) Appl. No.: 12/223,369

(22) PCT Filed: Jan. 30, 2007

(86) PCT No.: PCT/US2007/002700
§ 371 (c)(1),
(2), (4) Date: Nov. 26, 2008

(87) PCT Pub. No.: WO2007/089868
PCT Pub. Date: Aug. 9, 2007

(65) Prior Publication Data
US 2009/0317832 A1    Dec. 24, 2009

Related U.S. Application Data

(60) Provisional application No. 60/763,962, filed on Jan. 31, 2006.

(51) Int. Cl.
*G01N 33/53* (2006.01)
*A61K 49/00* (2006.01)
*A61K 39/395* (2006.01)
*G01N 33/569* (2006.01)

(52) U.S. Cl.
CPC .............. *G01N 33/56972* (2013.01); *G01N 2333/70514* (2013.01)
USPC ....... 435/7.1; 424/9.1; 424/130.1; 424/172.1; 424/173.1

(58) Field of Classification Search
None
See application file for complete search history.

(56) References Cited

U.S. PATENT DOCUMENTS

2004/0110122 A1\* 6/2004 Kasinrerk ................. 435/4

FOREIGN PATENT DOCUMENTS

WO    WO-03/069421 A2    8/2003
WO    WO-2004/106535    12/2004

OTHER PUBLICATIONS

Gennaro et al., (Clinical and Diagnostic Lab. Immunol. 1997. vol. 4(2):195-201).\*
Barnett et al., (Clin Lab. Haem. 1997. vol. 19:231-241).\*
Schnizlein-Bick et al., (Cytometry (Clinical Cytometry) 2002. vol. 50:46-52).\*
O. Siiman et al., "Immunophenotyping Using Gold or Silver Nanoparticle-Polystyrene Bead Conjugates with Multiple Light Scatter", *Cytometry*, vol. 41, pp. 298-307 (2000).
G. Janossy et al., "Precise CD4 T-Cell Counting Using Red Diode Laser Excitation: For Richer, for Poorer", *Cytometry*, vol. 50, pp. 78-85 (2002).
G. Janossy et al., "Affordable CD4$^+$ T-cell counts on 'single-platform' flow cytometer I. Primary CD4 gating", *British Journal of Haematology*, vol. 111, pp. 1198-1208 (2000).

\* cited by examiner

*Primary Examiner* — Rod P Swartz
(74) *Attorney, Agent, or Firm* — Edwards Wildman Palmer LLP; George W. Neuner; Christopher R. Cowles

(57) ABSTRACT

The present invention involves the reaction of a CD4 immuno-conjugate with a sample of patient whole blood. The CD4 immuno-conjugate consists of one or more antibodies with specificity for the CD4 surface receptor coupled to a signal moiety, or "label", that is detectable by a flow cytometer. Such labels may generate a signal by such means as fluorescence properties, light scatter properties, electronic properties, or magnetic properties. The CD4 immuno-conjugate binds to both the CD4 positive lymphocytes (Helper T cells) and all monocytes. Differential detection means are employed to count immuno-conjugate labeled Helper T cells. The present invention distinguishes itself by simultaneously measuring the signal level from monocytes as a means to verify sufficient activity of the anti-CD4 antibody.

2 Claims, 1 Drawing Sheet

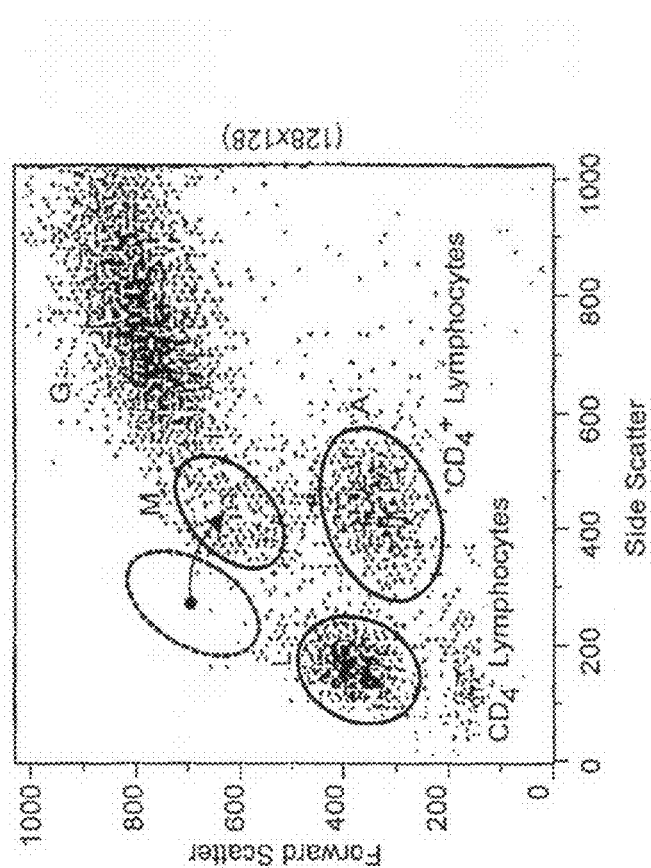

FIG. 1B

Same blood sample as FIG. 1A, but using immunogold conjugate to label CD4 cell surface receptor. The lymphocyte cluster splits into $CD_4^-$ and $CD_4^+$ lymphocyte. The entire monocyte cluster is labeled and shifts to the right (arrow).

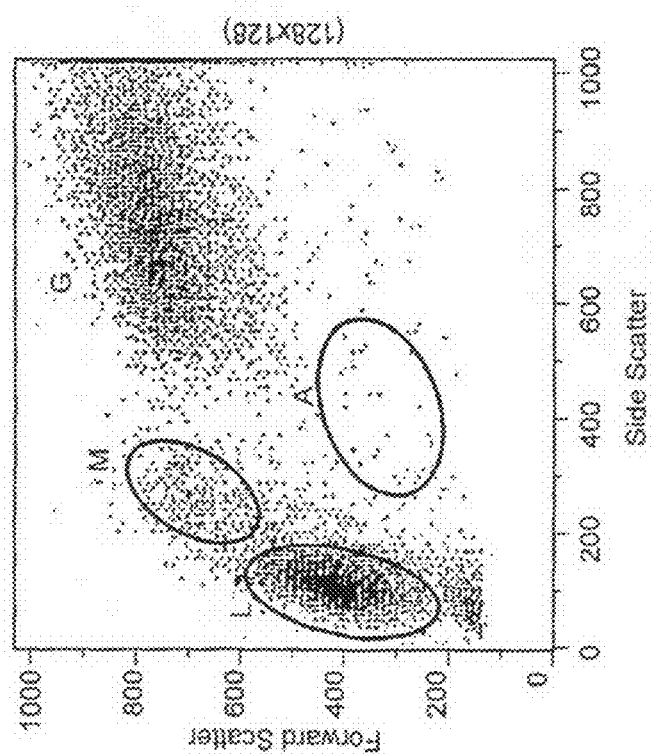

FIG. 1A

Blood sample with red cells removed by lysis. Lymphocyte (L), Monocyte (M), and Granulocyte (G) clusters are shown. No immunogold conjugate used.

CELL CLASSIFICATION SYSTEM

CROSS REFERENCE TO RELATED APPLICATION

The present application claims the benefit of U.S. provisional application No. 60/763,962, filed Jan. 31, 2006, which is incorporated by reference herein in its entirety.

FIELD OF THE INVENTION

This invention relates to the field of biological assays where cells can be classified and quantified using flow cytometry and other optical instrumentation. More specifically, the invention relates to the field of quality control of blood cell sub-population counting by flow cytometry when blood cell sub-populations are identified by binding labeled antibodies to cell surface antigens. These so-called "immuno-hematology" results are used most often to manage and prescribe drug therapy in HIV/AIDS.

BACKGROUND

At the time of this invention approximately 50 million people worldwide are infected by HIV, many of which are at a stage of their disease where antiretroviral drug therapy is medically indicated. Disease staging of HIV is done by counting specific immune cells in blood several times per year. These cells progressively decrease in number over a span of many years to a level where immunity is impaired and fatal opportunistic infection occurs. This condition is known medically as AIDS. When cell counting is used to monitor specific immune cells in blood and the results are used to time the administration of antiretroviral therapy, the procedure is 90% successful in establishing remission that lasts for several years. Without this the rate of remission is only approximately 20%. It is now an unquestioned axiom that immune cell counting must guide antiretroviral therapy in treating HIV.

It is estimated that 95% of individuals infected with HIV live in regions where skilled laboratory staff do not exist. These are needed to operate "flow cytometers", which are the instruments used to count immune cells. Flow cytometers are classified as highly complex systems by most regulatory agencies because they need many skilled manual steps to prepare patient blood samples, and they are mechanically and electronically unstable, requiring careful adjustment during the day. The training time for a flow cytometry operator is measured in years. The rate at which the HIV infection epidemic has grown and established a death rate that is now estimated to be 6,000 per day, has bested all efforts to create sufficient numbers of technicians and flow cytometry centers in the less developed parts of the world.

Automation with internal hardware and software checks, such as that developed for the PointCare AuRICA system (PointCare Technologies, Inc., Marlborough, Mass. USA), has eliminated all of the manual steps needed to prepare samples for flow cytometry analysis. This would have a major impact on the level of training needed for flow cytometer operation if it were not for two, remaining difficult problems. The first is training operators to use so-called external control materials (assayed artificial or surrogate blood samples) to verify that the flow cytometer is actually functioning within specification at the beginning and/or end of each day. The second is that these external control materials require an uninterrupted "cold chain" for shipment and storage. Maintaining a cold chain requires training and a refrigeration infrastructure that is generally missing in the rural developing world. The critical path to develop a flow cytometer that can be used by staff with minimal training in resource-poor areas lies along the elimination of external control materials.

In immune status testing, the primary role of external control materials is to assure that the unstable, temperature sensitive, antibodies that are used as reagents to bind to cell surface antigens and classify cells for counting, have retained their chemical binding capacity. It is not enough to know that the right concentration of reagent antibody is used. In fact, both the concentration and the binding activity must be assured for this key reagent. Antibodies are heat labile proteins that are easily damaged after a few hours in a non-air-conditioned laboratory. When that happens, flow cytometry cell counts will be wrong.

The primary problem with external controls for most of the world is that they are as temperature sensitive as antibodies. They need to be shipped under refrigeration, and rarely last more than one month even under careful re-refrigeration once the container is opened. Reliable refrigeration is not always available and this creates logistical problems for remote clinics and a need for well trained logistics personnel in the clinic. Secondarily, external controls are expensive. Some small clinics need to spend more money to run external controls than to run patient samples. Thirdly, quality is only assured for patient samples run during a specified time after an external control sample is run. It would be advantageous if quality could be assured for every patient sample irrespective of when the sample is run.

The subject of this invention is a method and apparatus that uses the patient's own blood cells during the sample run rather than surrogate, external control materials to check antibody concentration and activity. The blood cells used as an "internal control" are not the ones that decline in numbers during the course of HIV disease progression. The internal controls cells are an immune cell class that carry the same binding sites for antibody as do the immune cell class whose population is affected by HIV. These cells provide a means to control antibody concentration and activity that is independent of the disease and avoids the cost of external control materials. Additionally it provides the advantage of providing a simultaneous, "internal control material" check during every patient sample run; an option that is neither financially feasible nor technically feasible with external control materials.

SUMMARY OF THE INVENTION

The primary classes of circulating white blood cells are lymphocytes, monocytes, neutrophils, eosinophils, and basophils. Each are participants in various, complex, disease defense mechanisms; and deviations from a normal, or disease free condition, relationship of relative numbers between the subsets is highly correlated with specific disease states. During the time course of HIV progression to full-blown AIDS, a subclass of lymphocytes is destroyed eventually creating an immune-compromised state where the patient is open to a variety of opportunistic infections and cancer that prove fatal.

The subclass of lymphocytes destroyed by HIV infection is one which carries 94,000±28,000 surface receptors per cell known as the CD4 receptor (Bikoue, A., et al, Cytometry 1996; 26: 137). Various names have been attached to this subclass; the most common are the "Helper T cell" subclass and the "CD4+ lymphocyte" subclass. At the time of this invention an HIV infected patient passes into the clinical stage of "full-blown AIDS" when the Helper T cell count falls to 200/μl. After this the patient's immune defense is all but lost and death ensues from irreversible opportunistic infection (e.g., tuberculosis) or cancer (Kaposi's sarcoma).

The class of circulating white blood cells actually infected by actual virus (HIV), is however the monocytes and is not the lymphocytes. Indirect, intercellular signaling paths acting between infected monocytes and Helper T cells cause the destruction of the Helper T cells (Fantuzzi, L., Leuk. Biol. 2003; 74:719). While monocytes may harbor the virus, their numbers are not affected by the virus.

Two facts are important for the present invention. First, all monocytes carry the same CD4 surface receptor as do Helper T cells. An ancillary fact is that the number of CD4 receptors on monocytes is 34,000±10,000 per cell (Bikoue, A., et al, Cytometry 1996; 26: 137) which is lower than that on lymphocytes. Second, the number of monocytes remains essentially constant and the number of CD4 receptors on monocytes also remains essentially constant throughout the course of HIV infection.

The present invention involves the reaction of a CD4 immuno-conjugate with a sample of patient whole blood. The CD4 immuno-conjugate consists of one or more antibodies with specificity for the CD4 surface receptor coupled to a signal moiety, or "label", that is detectable by a flow cytometer. Such labels may generate a signal by such means as fluorescence properties, light scatter properties, electronic properties, or magnetic properties. The CD4 immuno-conjugate binds to both the CD4 positive lymphocytes (Helper T cells) and all monocytes. Differential detection means are employed to count immuno-conjugate labeled Helper T cells. The present invention distinguishes itself by simultaneously measuring the signal level from monocytes as a means to verify sufficient activity of the anti-CD4 antibody.

BRIEF DESCRIPTION OF THE DRAWINGS

FIG. 1A shows a blood sample with red cells removed by lysis. Lymphocyte (L), Monocyte (M), and Granulocyte (G) clusters are shown. No immunogold conjugate used. Oval "A" shows the position of the shifted CD4+ lymphocyte cluster of FIG. 1B.

FIG. 1B shows the same blood sample as FIG. 1A, but using immunogold conjugate to label CD4 cell surface receptor. The lymphocyte cluster splits into CD4− and CD4+ lymphocyte. The entire monocyte cluster is labeled and shifts to the right (see arrow). Oval "A" shows the position of the shifted CD4+ lymphocyte cluster.

DETAILED DESCRIPTION OF THE INVENTION AND EXEMPLIFICATION

Since individual immuno-conjugate entities (antibodies plus label) are selected from the reaction mixture by a diffusion process, they bind randomly to lymphocytes or monocytes. This means that there is no preferred binding target, and a sampling of antibody binding efficacy to monocytes can be used as an unbiased indicator to infer antibody binding efficacy to lymphocytes when both binding pathways occur simultaneously in the same reaction mixture.

An example of this method is illustrated in FIGS. 1A and 1B. A standard research flow cytometer (Beckman Coulter Epics) was set up and used as follows. Light scatter detectors were enabled to detect scattering at a low forward angle (narrow cone of light centered at ~2 degrees off axis) and at substantially a right angle (wide cone of light centered at 90 degrees off axis). A standard, two-parameter, flow cytometry "dot plot" data display was used for data interpretation and analysis (FIGS. 1A and 1B). The forward scatter (FS) signal strength from each cell was recorded on the Y axis of FIGS. 1A and 1B and the right angle scatter (SS) signal strength from each cell was recorded on the X axis. The dots in the plot are the X-Y coordinates of the signal strength from each cell.

The example in FIGS. 1A and 1B used a whole blood sample from a healthy human donor. In FIG. 1A, the red cells were removed by lysis and the sample was run without an immuno-conjugate. The following interpretation is well-known in the art (Shapiro, H.; Practical Flow Cytometry, Ed. 4, Wiley-Liss, p 483). Three clusters of dots (cell signals) are seen. The approximately vertical, oval cluster at the lower left is contains only lymphocytes. The diffuse and less dense cluster to the upper right of the lymphocytes contains only monocytes. The approximately horizontal oval cluster contains only granulocytes.

In FIG. 1B, the same sample was run again, but this time after reaction with an "immunogold" conjugate. This conjugate consists of approximately 80 nm diameter colloidal gold particles coated by mouse monoclonal antibodies specific to the CD4 receptor. United States Patent Application Number 20040246480 describes the use of these conjugates for the detection and counting of Helper T cell identification and counting. As explained in this patent application, a second oval cluster is created by those lymphocytes that have bound the immunogold conjugate to the cell surface. Such binding creates substantially increased right angle scatter (SS) and a smaller change in forward scatter (FS).

Also referring to FIG. 1B, it is apparent that all monocytes have also bound the immunogold conjugate as evidenced by the fact that the entire monocyte cluster has shifted to the right along the SS axis. The original X axis position of the unlabeled monocyte cluster was $X=260$, and the shifted position was $X=450$. The ratio of X positions was therefore $(450/260)=1.73$.

For comparison the lymphocyte cluster shifted from $X=108$ to $X=428$. The ratio of X positions was therefore $(428/108)=3.96$.

Finally, note that the ratio of the monocyte shift to the lymphocyte shift which is $(1.73/3.96)=0.44$ compares favorably to the ratio of CD4 receptors on monocytes to lymphocytes $(34,000/94,000)=0.36±0.15$ (The standard error in this ratio was computed by propagating the independent errors in the above reported measurements of CD4 antigen numbers for lymphocytes and monocytes in the literature). This indicates that the degree of shifting is related to the number of antigen binding sites on these two cell populations.

This example illustrates the shift in the monocyte cluster caused by binding of anti-CD4 antibody conjugates. Additionally the magnitude of the monocyte cluster shift relative to the lymphocyte shift compares well with the ratio of the number of immunogold conjugates estimated from the literature to be bound to monocytes and lymphocytes respectively.

It is also possible to use the relative position (rather than the absolute position) of the monocyte cluster with respect to other clusters as a means to monitor anti-CD4 antibody binding to monocytes. In the above example and referring to FIG. 1, the position of the monocyte cluster relative to the granulocyte (neutrophil) cluster changes when anti-CD4 antibodies bind to the monocytes. The granulocyte cluster position is itself unaffected by the presence of anti-CD4 antibody. This is because virtually no granulocytes (neutrophils) carry the CD4 receptor. Therefore the reference for monocyte cluster can be the invariant granulocyte cluster which obviates the need for a reference measurement without anti-CD4 antibody. This preferred mode saves time to produce a patient result.

It is important to note that these observations can be employed to monitor antibody binding quality on a very high percentage of patient samples even when Helper T cells have been completely eliminated from the circulation in advanced AIDS. Monocytes and granulocytes (neutrophils) continue to circulate throughout the course of AIDS and the above illustration is an example of how they can be used as "sensors" for CD4 immuno-reagent activity.

The above example illustrates that the monocyte cluster shift relative to a reference can be used as an internal control at no added cost and no added training to check for anti-CD4 antibody conjugate activity on virtually every patient sample that is run. This is a significant improvement over the use of external control materials that are conventionally run only once per day. External control materials are expensive, and running them more frequently than once per day is financially prohibitive in resource poor (and resource rich) settings.

What is claimed is:

1. An internal quality control method for determining antibody binding capacity when counting CD4+ lymphocytes in a blood sample containing monocytes and granulocytes, the method comprising the steps of:
   a. reacting a reagent comprising a labeled antibody specific to the CD4 cell surface antigens with a first portion of a blood sample;
   b. analyzing by flow cytometry first signals in the form of a first dot plot from said labeled antibody reacted with the CD4 cell surface antigens on the lymphocytes and monocytes and differentially determining whether said signals emanate from lymphocytes or monocytes to determine a position of a first monocyte cluster;
   c. determining a first X-Y coordinate position of the first monocyte cluster;
   d. analyzing by flow cytometry second signals in the form of a second dot plot from a non-labeled second portion of the blood sample, and differentially determining whether said signals emanate from lymphocytes or monocytes to determine a position of a second monocyte cluster;
   e. determining a second X-Y coordinate position of the second monocyte cluster;
   f. determining a cluster that has not shifted position form by comparing the first dot plot with the second dot plot, thereby identifying a cluster of granulocytes; and
   g. determining a shift in the position of the labelled monocyte cluster from the position of the non-labelled monocyte cluster by comparing the first and second X-Y coordinate positions;
   thereby determining the activity of said labeled antibody and eliminating the need for an external control.

2. The method of claim 1, wherein the label emits fluorescent light or scattered light.

* * * * *